(12) United States Patent
Samsoondar et al.

(10) Patent No.: US 6,268,910 B1
(45) Date of Patent: Jul. 31, 2001

(54) METHOD AND APPARATUS FOR SCREENING PLASMA FOR INTERFERENTS IN PLASMA FROM DONOR BLOOD BAGS

(75) Inventors: James Samsoondar, Cambridge; Douglas George Given, Waterloo, both of (CA)

(73) Assignee: CME Telemetrix Inc., Waterloo (CA)

( * ) Notice: Subject to any disclaimer, the term of this patent is extended or adjusted under 35 U.S.C. 154(b) by 0 days.

(21) Appl. No.: 09/367,863

(22) PCT Filed: Mar. 3, 1998

(86) PCT No.: PCT/CA98/00170
§ 371 Date: Sep. 3, 1999
§ 102(e) Date: Sep. 3, 1999

(87) PCT Pub. No.: WO98/38961
PCT Pub. Date: Sep. 11, 1998

Related U.S. Application Data
(60) Provisional application No. 60/038,555, filed on Mar. 3, 1997.

(51) Int. Cl.[7] .................................................. G01N 33/48
(52) U.S. Cl. ............................................. 356/39; 356/40
(58) Field of Search .............................. 356/39, 43, 364, 356/73, 40; 374/159, 161, 126; 604/27, 28, 39, 43, 54, 66, 67, 320, 325; 128/637, 638, 760, 7

(56) References Cited

U.S. PATENT DOCUMENTS

| 4,522,494 | 6/1985 | Bonner | 356/39 |
|---|---|---|---|
| 4,675,019 | 6/1987 | Bellhouse | 604/408 |
| 4,707,147 | * 11/1987 | Aoki et al. | 374/161 |
| 5,029,584 | * 7/1991 | Smith | 128/638 |
| 5,066,859 | 11/1991 | Karkar | 250/339 |
| 5,288,646 | 2/1994 | Lundsgaard | 436/165 |
| 5,291,884 | 3/1994 | Heinemann | 128/633 |
| 5,351,685 | 10/1994 | Potratz | 128/633 |
| 5,353,790 | 10/1994 | Jacques | 128/633 |
| 5,360,004 | 11/1994 | Purdy | 128/633 |
| 5,366,903 | 11/1994 | Lundsgaard | 436/165 |

FOREIGN PATENT DOCUMENTS

| 0 706 043A | 4/1996 | (EP) . |
|---|---|---|
| 195 30 969 | 2/1997 | (EP) . |

* cited by examiner

Primary Examiner—Frank G. Font
Assistant Examiner—Michael P. Stafira
(74) Attorney, Agent, or Firm—Bereskin & Parr

(57) ABSTRACT

An apparatus and a method whereby plasma integrity of plasma contained in a blood bag is rapidly and accurately assessed without compromising the sterility of the plasma, or destroying any of its components. This is achieved through spectral data which is used in a novel way so as to determine if a plasma specimen representative of plasma in a blood bag contains interferents and if so, to what extent. The apparatus and method analyse plasma contained in two bags whereby tubing connects the two bags. A lamp is used to irradiate the specimen, and a spectrophotometer is used to measure radiation from the specimen. The apparatus and method allow for determination where both the bags and tubings are translucent and contain writing on their surfaces (e.g., proprietary information), and the light is transmitted through the writings, plastic, and the plasma contained in the bag or tubing.

23 Claims, 15 Drawing Sheets

METHOD AND APPARATUS FOR SCREENING PLASMA FOR INTERFERENTS IN PLASMA FROM DONOR BLOOD BAGS

This application claims benefit of Provisional Application PCT No. 60/038,555 filed Mar. 3, 1997.

FIELD OF INVENTION

This invention relates to spectrophotometry and the spectrophotometric analysis of plasma expressed from donor blood bags. In particular, this invention relates to a method and apparatus for providing a rapid non-destructive measurement of substances called interferents which compromise plasma integrity, by measurement of absorbance or reflectance. Furthermore, the spectrophotometric measurements are made after the plasma is expressed from the primary blood donor bags, without altering the sterility of the blood components.

BACKGROUND OF INVENTION

Blood is usually donated into sterile plastic bags which contain anticoagulants. These bags ("blood bags") are connected to one or more similar bags by plastic tubing in a closed system for maintaining sterility. After centrifugation of whole blood contained in a primary collection bag, plasma or plasma plus platelets can be separated from red blood cells in the bag: a higher centrifugal force can separate all cellular elements from the plasma, and a lower centrifugal force can separate the plasma plus platelets from the red cells; the plasma plus platelets can then be subjected to higher centrifugal force in order to separate the platelets from the plasma. Therefore, if separation of plasma, platelets, and red cells is required, a two-step centrifugation is necessary, with a primary blood bag linked to two "satellite" bags in series. If separation of all cellular elements from plasma is required, a single-step centrifugation is necessary, with the primary blood bag linked to one satellite bag. In both cases, plasma will be contained in the last bag having transferred to this last blood bag via plastic tubing from the other bags.

Plasma is used frequently for transfusion to treat clotting disorders, to expand blood volume, to treat shock due to plasma loss in burns or hemorrhage. Plasma is also used frequently to prepare plasma substances, e.g., clotting factors, and other proteins like albumin. This process is referred to as plasma fractionation. The plasma used must not have excessive amounts of hemolysis, turbidity or bile pigments. Since donors are usually healthy, elevated bile pigments is not expected.

Blood chemistry tests are routinely performed on the serum or plasma of whole blood. In a routine assay, red blood cells are separated from plasma by centrifugation, or red blood cells and various plasma proteins are separated from serum by clotting prior to centrifugation. Many tests conducted on plasma or serum samples employ a series of reactions which terminate after the generation of chromophores which facilitate detection by spectrophotometric measurements at one or two wavelengths. Elevated Hb in the blood, i.e., haemoglobinemia, can be due to disease states and as a result of specimen collection and handling. Elevated bile pigments can be due to disease states. Increased lipid particles in the blood, also known as hyperlipidemia, can be due to disease states and dietary conditions.

Measurement of interfering substances prior to conducting such blood tests is important in providing meaningful and accurate test results. Haemoglobin (Hb), bile pigments, namely bilirubin (BR) and biliverdin (BV) and light-scattering substances like lipid particles are typical substances which will interfere with, and affect spectrophotometric and other blood analytical measurements. Such substances are referred to as interferents. Although blood is screened for the presence of several viruses, there is no test which provides 100% assurance of the absence of these viruses, and there are still other harmful viruses which are never tested for. In order to increase assurance that harmful viruses are eradicated if present, viral inactivation processes are being developed. One method used for inactivating viruses in plasma is the addition of methylene blue (MB) to the plasma. MB is highly chromogenic and must also be regarded as an interferent. In fact, if a sample is sufficiently contaminated with interferents, tests are normally not conducted as the results will not be reliable.

In blood banking, plasma with compromised integrity will be discarded. Plasma specimen integrity is an essential part of quality assurance as it directly affects the accuracy of test results, and the suitability of the plasma for transfusion or fractionation. Measurement of MB provides additional assurance that the plasma contains the required amount of MB.

Spectrophotometric measurement typically employs infrared (IR) or near infrared radiation (NIR) to assess the concentration of various constituents in a blood sample. Examples of photometric measurements using containers which hold a blood sample are disclosed in U.S. Pat. Nos. 5,291,884; 5,288,646; 5,066,859; and 5,366,903.

U.S. Pat. No. 5,366,903 discloses a sampling device which allows photometric quantitative determination of an analyte in whole blood. The device overcomes the problems of having blood cells in a blood sample by effectively "squeezing out" red blood cells and providing a small volume of sample, free of red blood cell material, from which particular analytes can be measured.

Other applications of photometric methodology include non-invasive determinations of analyte concentrations such as described in U.S. Pat. Nos. 5,360,004; 5,353,790; and 5,351,685. DE 195 30 969A describes a system in which blood contained in a bag is passed to a satellite bag for separation of thrombocyte concentrate from the rest of the plasma. A photometer 10, 18 is used to detect when the first eryathrocytes arrive thereat, at which time valve 8 is closed. EP 0 706 043A discloses the spectroscopic measurement of a liquid sample contained in a transparent plastics bag 14 using optical fibre bundles to lead light into and out from the bag support 12. U.S. Pat. No. 4,522,494 relates to the assessment of the viability of platelets in a transparent flexible blood storage bag. Light from a laser beam is passed into the bag, supported between glass plates 18, 24, and scattered light is measured. U.S. Pat. No. 4,675,019 describes a blood bag having tablets attached to the walls to define an optical path through which light can be passed to measure platelet viability. However none of these documents discloses a method of measuring interferents in the plasma or serum of a blood sample, in order to assess specimen integrity with respect to blood tests, plasma transfusion, or plasma fractionation.

Current methods used for detecting haemoglobinemia, bilirubinemia, biliverdinemia and lipemia or turbidity utilize visual inspection of the specimen with or without comparison to a coloured chart. It is to be understood that those practising in the field use the terms lipemia and turbidity interchangeably. This is because lipemia is the major cause of turbidity in serum or plasma. In blood banking, turbidity is assessed by the ability to read print on a paper placed behind a plasma bag.

Screening of plasma specimens by visual inspection is semi-quantitative at best, and highly subjective. Furthermore, visual inspection of plasma specimens is a time consuming, rate limiting process. Consequently, state-of-the-art blood analyzers in fully and semi-automated laboratories, and automated blood banking facilities cannot employ visual inspection of specimens.

Other methods to assess specimen integrity employ direct spectrophotometric measurement of a diluted sample in a special cuvette. However, such methods are not rapid enough for screening samples. In order to obtain a measurement of the sample of the plasma or serum, specimen tubes must be uncapped, a direct sample of the specimen taken and diluted prior to measurement. Each of these steps is time-consuming and requires disposable cuvettes. In blood banking, sterile techniques must be practised, especially when blood products are not used promptly. Maintaining a closed system is necessary to avoid bacterial contamination, hence any screening for interferents must be performed with the bag-tubing system intact. Removing a segment of the tubing linking the blood/plasma bags by heat-sealing can be performed without altering the sterility of the blood products, but this too is time consuming. Therefore, a rapid and effective method for measuring interferents in plasma in the blood banking industry is required.

SUMMARY OF THE INVENTION

It is desirable to provide an apparatus and a method whereby plasma integrity of plasma contained in a blood bag is rapidly and accurately assessed without compromising the sterility of the plasma, or destroying any of its components.

In one aspect of the invention, spectral data is used in a novel way so as to determine if a plasma specimen representative of plasma in a blood bag contains interferents and if so, to what extent.

In another aspect of the invention, there is provided an apparatus and a method for determining plasma integrity where the plasma is contained in two bags and tubing connects two bags using a lamp to irradiate the specimen, and a spectrophotometer to measure radiation from the specimen.

In still another aspect of the invention, both the bags and tubings are translucent and contain writing on their surfaces (e.g., proprietary information), and the light is transmitted through the writings, plastic, and the plasma contained in the bag or tubing.

In yet another aspect of the invention, there is provided an apparatus and a method for determining plasma integrity, where the light is reflected from a reflective surface placed behind the plasma bag or the tubing connecting the bags.

In another aspect of the invention, plasma integrity of plasma contained in a blood bag is assessed by measuring:

1. Haemoglobin concentration as an assessment of haemolysis;
2. Bilirubin concentration as an assessment of bilirubinemia;
3. Biliverdin concentration as an assessment of biliverdinemia;
4. Equivalent intralipid concentration for the assessment of turbidity; and
5. Methylene blue concentration as part of the viral inactivation quality assurance system.

In one embodiment, Hb concentration is determined by measurement of absorption of different wavelengths of light in plasma specimens contained in a blood bag which are then compared with values obtained through calibration using reference measurements for haemoglobin in plasma specimens. Turbidity, in equivalent grams per liter Intralipid™ (IL), is determined by measurement of absorption of different wavelengths of light in the blood bag plasma specimens which are then compared with values obtained through calibration using serum samples spiked with known amounts of IL; IL is a fat emulsion in water which is similar to naturally-occurring chylomicrons, and may be used to simulate turbid serum or plasma specimens. BR concentration is determined by a combined measurement of absorption of different wavelengths of light in the blood bag plasma specimens which are then compared with values obtained through calibration using reference measurements for BR in plasma samples. BV concentration is determined by a combined measurement of absorption of different wavelengths of light in these plasma specimens which are then compared with values obtained through calibration using reference measurements for BV in plasma samples. MB concentration is determined by measurement of absorption of different wavelengths of light in these plasma specimens which are then compared with values obtained through calibration using reference measurements for MB in plasma specimens. On the basis of the results from measurements of any one or more of these interferents at a time, in comparison with reference measurements of various levels of interferents, a decision is made concerning whether to reject or accept the plasma. Instead of using a reference measurement for a substance, its actual concentration can be calculated from the known amount that was added.

In another embodiment, light is allowed to be reflected off a reflecting surface which must be placed directly behind the plasma sample contained in a blood bag. Hb concentration is determined by measurement of reflectance of different wavelengths of light in the blood bag plasma specimens which are then compared with values obtained through calibration using reference measurements for haemoglobin in serum or plasma samples. Turbidity, in equivalent g/L IL, is determined by measurement of reflectance of different wavelengths of light in plasma specimens which are then compared with values obtained through calibration using serum samples spiked with known amounts of IL. BR concentration is determined by a combined measurement of reflectance of different wavelengths of light in plasma specimens which are then compared with values obtained through calibration using reference measurements for BR in plasma samples. BV concentration is determined by a combined measurement of reflectance of different wavelengths of light in plasma specimens which are then compared with values obtained through calibration using reference measurements for BV in plasma samples. MB concentration is determined by measurement of reflectance of different wavelengths of light in plasma specimens which are then compared with values obtained through calibration using reference measurements for MB in plasma specimens. On the basis of the results from measurement of any one or more of these interferents at a time, in comparison with reference measurements of various levels of interferents, a decision is made concerning whether to reject or accept the plasma contained in the blood bag.

In still another embodiment of the invention, a bag of plasma is placed in a box which houses a V-shaped receptor for a corner of the bag. Light is transmitted through the plasma in the bag, and the receptor maintains a constant pathlength across the walls of the "V," for any bag.

In yet a further embodiment the present invention provides an apparatus for determining plasma integrity of plasma where the apparatus comprises: a housing, which does not have to be light-tight, for receiving a sample; a radiation source; a spectrophotometer with appropriate filters, a grating and a linear photodiode array (PDA) detector; a means for optically connecting the radiation source with the detector along a sample path through the housing and along a reference path which by-passes the sample; a means for selectively passing a beam from the sample path and from the reference path to the detector; a means for selecting an appropriate integration time required for adequate detector response; and a means for correlating a detector response, from the sample path relative to a detector response from the reference path, to a quantity of a known substance in said sample.

The apparatus further comprises a quartz-tungsten-halogen bulb capable of emitting a near infrared, and adjacent visible region light beam having wavelengths from 475 nm to 1075 nm and a single optical fibre bundle which randomly samples light from the quartz-tungsten-halogen bulb. The single fibre bundle bifurcates into a sample path beam for travel along a sample path and a reference path beam for travel along a reference path. The bifurcated optical fibre consists of multiple fibres which focus random sampling of light from the lamp, into single fibres of 0.4 millimeter diameter for both the sample and reference beams. This apparatus further comprises two shutters, installed in the lamp assembly, for selectively blocking the sample path light beam which travels along the sample path through a sample enclosed in a housing, and the reference path light beam which travels along the reference path. The two light paths are collected into two fibres which converge into a single fibre which is focused onto the detector; the bifurcated collection optical fibre consists of multiple fibres. This apparatus further comprises a grating for dispersing the combined beam into component wavelengths which are passed onto the detector. The detector of this apparatus is a PDA comprised of a plurality of pixels wherein each of the pixels is set to measure one of a plurality of predetermined light frequencies. Based on the measurement of the frequencies, the detector generates a plurality of signals wherein each of the signals is responsive to an amount of radiation received by each of the pixels. This apparatus further comprises an analog-to-digital converter to generate digital information from the plurality of signals and a microprocessor, which is connected to the convertor, to correlate the digital information to a quantity of a known substance in the sample. In order to cover the 475 to 1075-nm wavelength range, one of two gratings must be used depending on in which range measurements are being taken: one grating provides 475–910 nm , and another grating provides 575–1075 nm . Calibration algorithms were developed for five interferents namely, haemoglobin, bilirubin, biliverdin, intralipid and methylene blue, based on wavelengths in the 475 to 910-nm range. However, if BR measurement is not required, the grating which provides 575–1075 nm can be used. In one aspect of the present invention, more than one calibration algorithm can be developed for the same interferent, using different wavelengths. This is exemplified by the two different calibration algorithms for IL, shown later.

In another aspect of the invention, a completely light-tight sample holder is not required. Rather, the apparatus contains a housing comprised of a stationary part which has a cavity for receiving a sample and a movable part which can close over the sample. The design of the apparatus eliminates most movement of the optical fibres during motion of the movable part of the sample holder. According to one embodiment, housing which holds tubing from a blood bag which housing is not completely light-tight: room light leakage occurs along the tubing which sticks out of the sample holder. A method of the invention provides that the light leakage is compensated for by measuring dark current, i.e., detector response when detector is not exposed to instrument light, for both sample and reference measurements. Two shutters in the apparatus are located in the lamp assembly, and are used for sequentially directing light through the sample or reference pathway. Since there is no shutter between the sample housing and the sensor, any room light leakage into the sample housing will affect sample light and sample dark scans equally when performed at the same integration time, and the reference light and reference dark scans when performed at the same integration time used for the reference measurements. Therefore, room light impinging on the detector can be effectively subtracted without affecting the performance of the apparatus, provided that the ambient light does not change during the few seconds measurement time.

In a further aspect of the present invention the apparatus provides a means for determining specimen integrity of a sample by determining the concentrations of a known substance which is selected from a group comprising haemoglobin, Intralipid, bilirubin, biliverdin, and methylene blue.

In yet a further embodiment of the present invention a method is provided for determining plasma integrity of plasma contained in a blood bag, wherein the method comprises the following steps. First, transmitting a beam of radiation along a sample path through a sample of the plasma and along a reference path by-passing the sample. Next, selectively receiving the beam of radiation from the sample path and the reference path, and analyzing the received beams of radiation from the sample path and from the reference path for an amplitude of at least one predetermined light frequency. Finally, correlating the absorbance of at least one predetermined light frequency with a quantity of a known substance.

In a further aspect of the present invention there is provided a method for determining plasma integrity of plasma contained in a blood bag, wherein the method allows for the determination of the concentrations of a known substance which is selected from a group comprising haemoglobin, bilirubin, Intralipid, biliverdin, and methylene blue.

DESCRIPTION OF THE INVENTION

Figure 1:
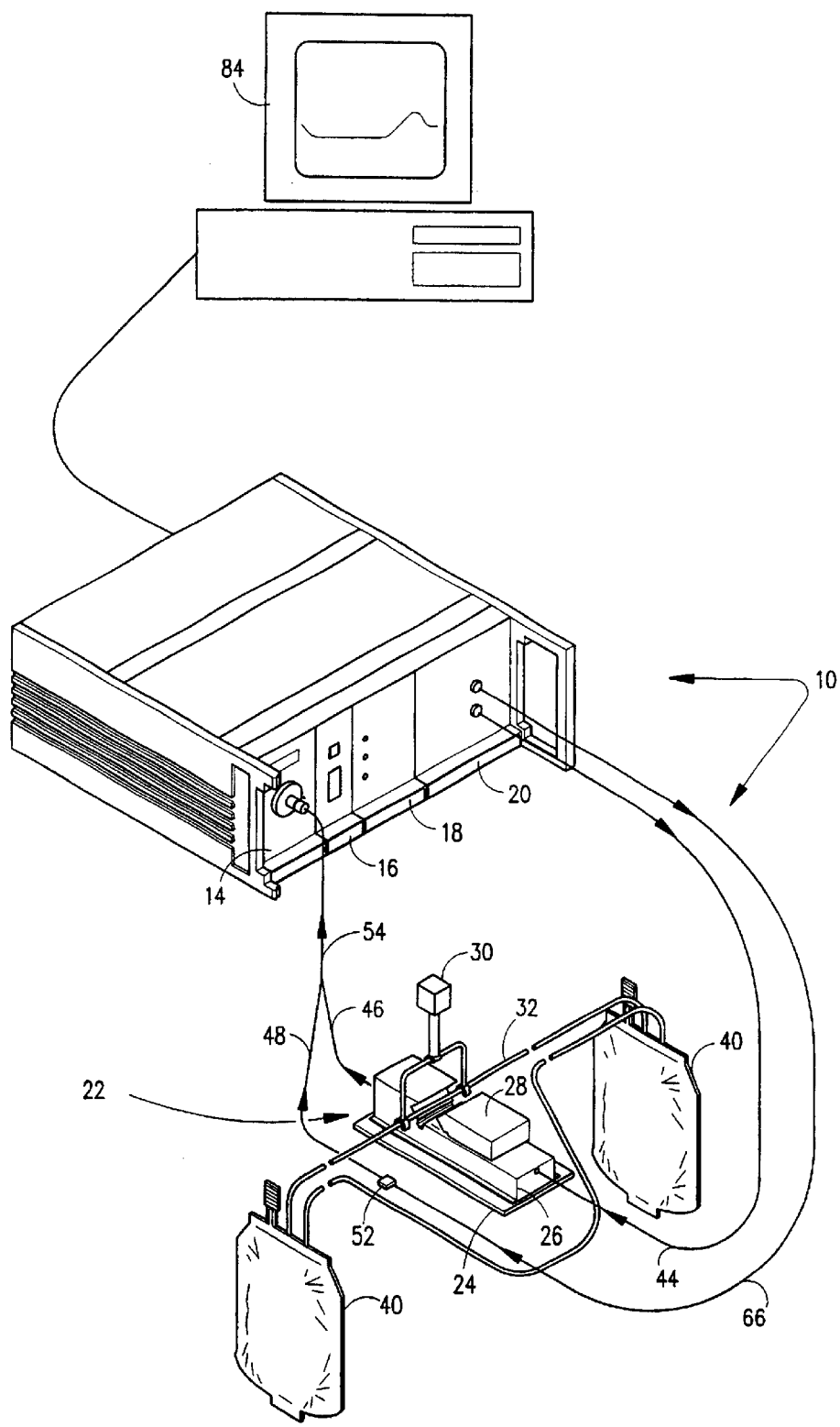
FIG. 1 is a perspective view of a system incorporating an apparatus of the present invention for analyzing plasma integrity of plasma contained in blood bags.

A system incorporating the apparatus of the present invention is generally shown in FIG. 1. The apparatus 10 comprises a spectrophotometer 14 optically coupled to a sample holder 22 through single optical fibres 44, 46. Sample holder 22, is shown in greater detail in FIGS. 2 and 3 and consists of a stationary part 26, and a movable part 28, mounted on a baseplate 24. Referring again to FIG. 1, apparatus 10 is mounted or installed adjacent to an automated blood banking system which carries two or more blood/plasma bags 40 linked by PVC or other flexible tubing 32. A robotic arm 30 is installed to transport a section of the tubing 32 into the sample holder 22. It is understood that other conveyor transport mechanisms for tubing could be employed, a part of the plasma bag can be used for sampling, and that all such variations are within the scope of the present invention. Furthermore, any means by which input and output fibre optic bundles are brought into alignment for measurement of absorption or reflectance in a plasma specimen container are within the scope of the present invention.

Sample fibres 44 and 46 direct radiation from a light source to and from the sample respectively, and allow the bulk of the instrumentation to be placed remotely from the plasma specimens. Multiple optical fibres 46 and 48 are the strands of a bifurcated optical fibre which collects radiation alternately from the sample and reference single optical fibre 66, and combines into one multiple optical fibre 54 which communicates with a spectrophotometer 14. Reference fibre 66 is joined to a strand 48 of the bifurcated fibre by a coupling 52.

After a sample is placed in holder 22, a sensor 34 will activate movable part 28 of the sample holder to close. Once in the closed position sample tubing 32 is held in cavity 42 of the sample holder. After a fixed time which is required for the sample holder to close, light is transmitted through sample contained in tubing 32. Along the side of the sample holder is a separate fibre 66 for transmitting reference light, when shutter 56 (see FIG. 4) at the sample channel is closed and shutter 58 at the reference channel is open. Sample and reference dark scans are also performed with the sample in place with the sample holder closed, and shutters 56 and 58 closed, using the integration times used for the respective light scans.

Figure 2:
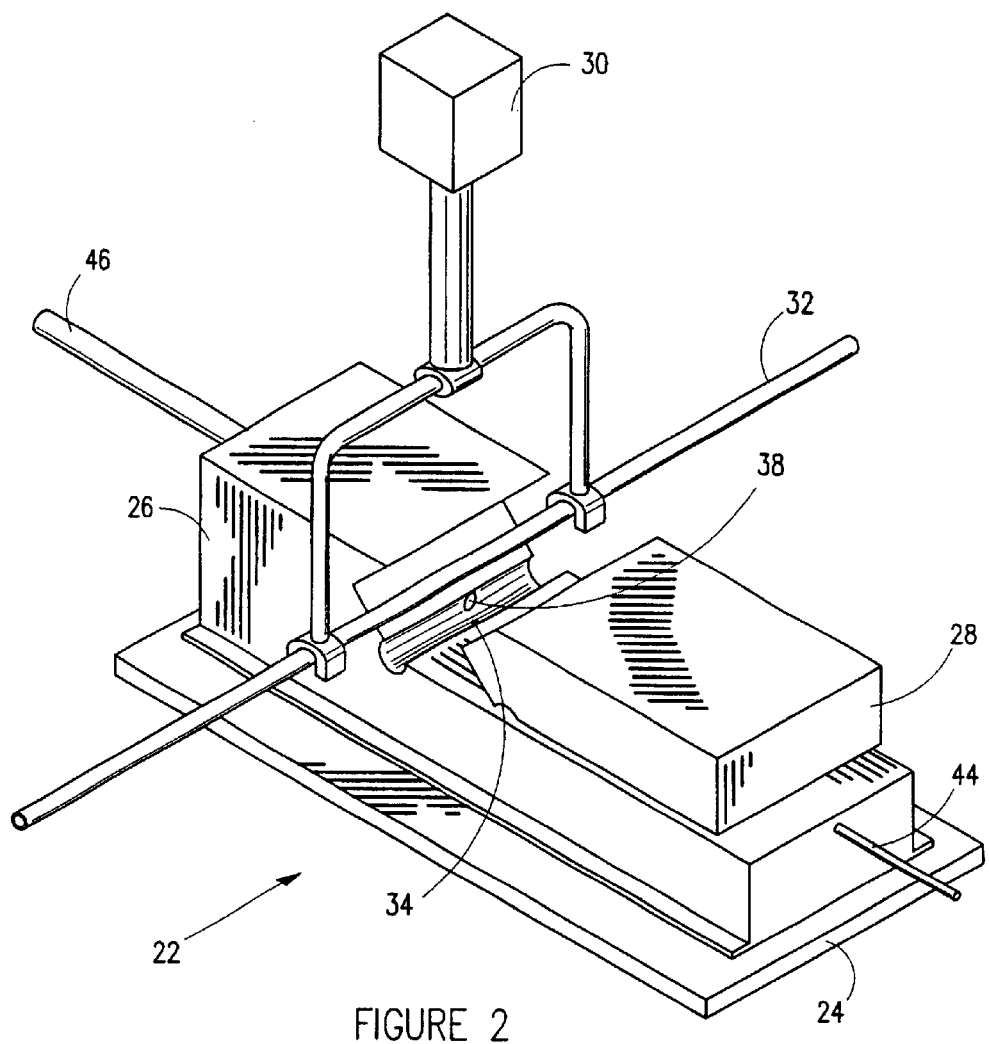
FIG. 2 is a perspective view of the sample holder of the apparatus of FIG. 1.
Figure 3:
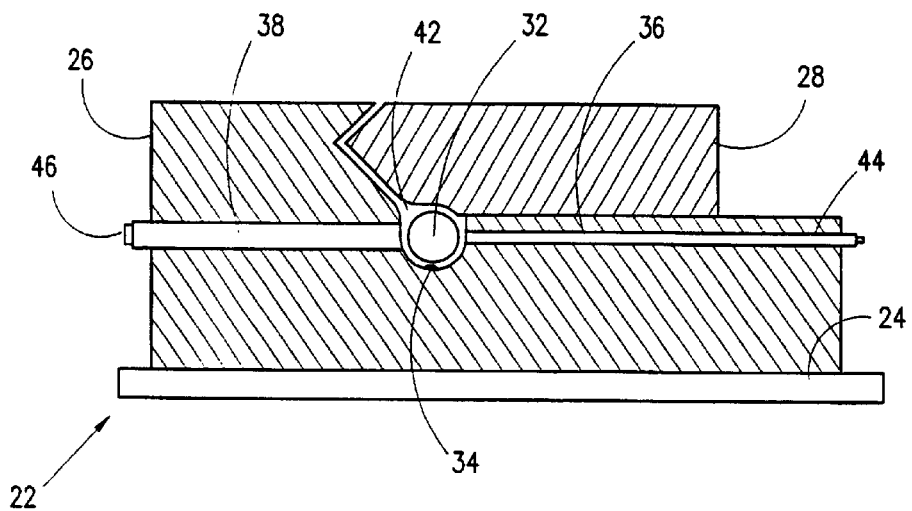
FIG. 3 is a longitudinal cross-sectional view of the sample holder of FIG. 1.

Referring to FIGS. 2 and 3, optical fibre 44 extends through a bore 36 in a wall of the sample holder as shown such that the end of optical fibre 44 communicates with cavity 42 to transmit radiation therein. Similarly, optical fibre 46 extends through a bore 38 in a wall of the sample holder opposite optical fibre 44. Fibre 46 communicates with cavity 42 to receive radiation impinging upon the portion of fibre 46 which communicates with cavity 42. In an alternative embodiment, optical fibers are arranged to permit measurement of reflected light in a sample.

Radiation is channelled through optical fibre 44 to the plasma specimen in a section of tubing 32, and the radiation transmitted through the tubing and markings on the tubing, and plasma specimen, is received by fibre 46, which returns collected radiation to spectrophotometer 14. In a preferred embodiment, fibres 44 and 66 are both 0.4 millimeter diameter, and referring also to FIGS. 1 and 4, fibre 48 is 1.6 millimeters, and fibre 46 is 0.5 millimeter. The reference fibres 66 and 48, which are of different diameters, are coupled together by a coupler 52. Although specific sizes of these fibres have been identified it is understood by those skilled in the art that other fibre sizes could be employed.

Referring to FIG. 1, the apparatus 10 includes a spectrophotometer 14, a central processing unit 16, a power supply 18, and a lamp assembly module 20.

Figure 4:
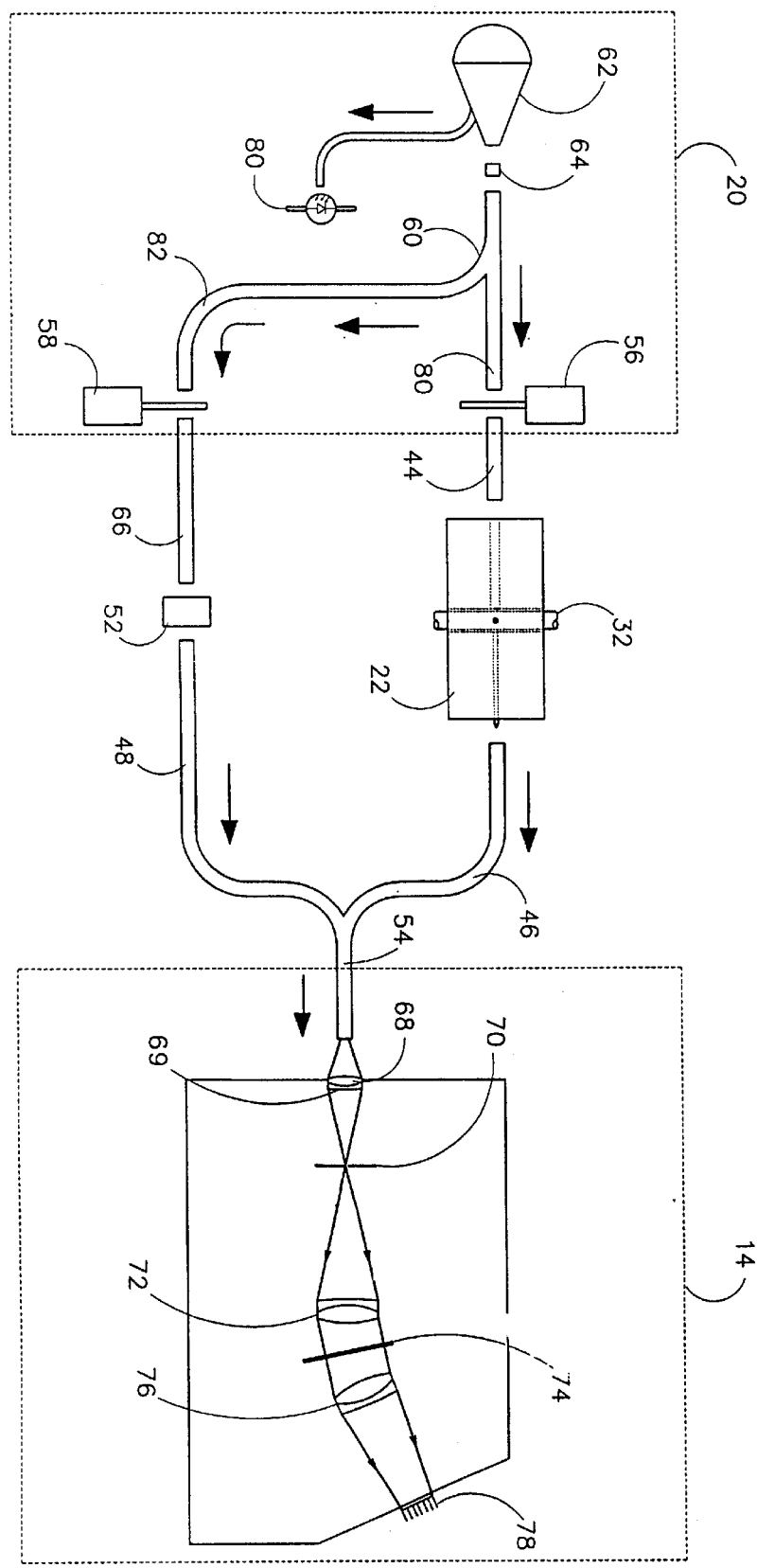
FIG. 4 is a schematic representation of elements of the apparatus of FIG. 1.

Referring to FIG. 4, the lamp assembly module 20 employs a light source 62. Preferably the light source is a quartz-tungsten-halogen 10 watt lamp, but other wattage lamps can be employed. The input power supply is alternating current, but the output to the light source is a stabilized direct current. Attached to the lamp is a photodetector 80, which monitors lamp output. Spectral output from light source 62 is broad band covering visible and NIR regions. Although the NIR region of the electromagnetic spectrum is generally considered to be the interval extending from 650 nm through to 2,700 nm, the nominal wavelength range of a preferred embodiment is from 475 nm to 1,075 nm, which is referred to herein as the "near infrared and adjacent visible region". The beam of radiation from light source 62 is directed through a band-pass filter 64 and shaping filter 69 in the spectrophotometer 14. The band-pass filter is required to reduce unwanted radiation outside of 575–1075 nm or 475–910 nm, depending on the grating used. The shaping filter is also required to "flatten" the detection system's optical response. It should be understood that a particular grating will provide a particular wavelength range, and the band-pass and shaping filters are specific for the wavelength range. All data presented in this specification used a grating which produced 575–1075 nm wavelength range, except for the bilirubin data which used the 475–910 nm wavelength range. In a preferred embodiment, the 475–910 nm wavelength range is used because this range can be used for all the analytes discussed. The beam of radiation from filter 64 is transmitted through a bifurcated multi-optical fibre bundle 60 to provide sample and reference beams. In a preferred embodiment the active area of bundle 60 is 5.25 millimeters diameter. Bifurcated bundle 60 provides random sampling of lamp radiation to supply the sample and reference beams via two arms of 60, 80 and 82 respectively. In a preferred embodiment, a balanced emerging radiation is provided to the PDA detector 78, from both the sample and reference paths, where 80 and 82 are 99% and 1% respectively, of the fibers of 60.

The sample and reference beams enter arms 46 and 48 respectively of a bifurcated multi- optical fibre bundle which combine in fibre 54 and are focused alternately onto a slit 70, by a focusing lens 68 and a shaping filter 69. Emerging radiation is collimated by lens 72 before the beam is directed to grating 74 which is a dispersing element which separates out component wavelengths. In a preferred embodiment dichromated gelatin is used as the grating material. Component wavelengths are focused by a lens 76, onto the PDA 78. Each element or pixel of the PDA is set to receive and collect a predetermined wavelength. In a preferred embodiment the PDA 78 comprises 256 pixels. The pixels are rectangular shaped to optimize the amount of optical radiation detected.

Spectrophotometer 14 is preferably a "dual-beam-in-time" spectrophotometer with a fixed integration time for the reference beam and a choice of integration time for the sample beam. Because the sample holder is not light-tight, sample and reference dark scans be subtracted from sample and reference light scans respectively; sample and reference dark scans are performed at the same integration times used for the respective light scans. In a preferred embodiment, the reference scan is performed at 13 milliseconds, and the sample scan is performed at 20 milliseconds; the maximum ADC value obtained at 20 milliseconds for a particular sample, is used to determine a new integration time up to 2600 milliseconds, such that saturation of the detector at any pixel does not occur. The maximum time allowed for any sample will depend on required speed of sample screening. Also, multiple scans can be averaged to minimize noise, but for the sake of speed in a preferred embodiment single scans are used.

When in use, each pixel or wavelength portion is measured approximately simultaneously during a particular scan. Optical radiation falling on each sensor element is integrated for a specified time and individual pixels or wavelengths are sampled sequentially by a 16 bit analog-to-digital convertor or ADC.

Although the present embodiment details use of a PDA, any alternative means which achieves the same result is within the scope of the present invention. For example a filter-wheel system may be used. In carrying out measurements each analyte uses from one to four wavelengths or pixels. Given that the first derivative of absorbance with respect to measurements with the PDA is the difference between the absorbance at two adjacent pixels, the first derivative of absorbance at one wavelength with a filter-wheel system will require absorbance measured with two different narrow band-pass filters. It will be readily understood by those skilled in the art that the filters do not need to be assembled on a rotating wheel, but that any structure which achieves the result of a narrow band-pass filtration of absorbed radiation is within the scope of the present invention.

Transmission is preferred over reflectance although either may be used. Variations in apparent absorbance due to markings on tubing can be accounted for by using the first derivative of apparent absorbance. The term "apparent" absorbance is used in connection with * when the amount of light transmitted through a sample is measured, and transmitted light is converted to absorbance units, as shown in the next paragraph; light attenuation by any means other than that which is absorbed by the sample will be interpreted as absorbance. For example, lipid particles will scatter light away from the detector, and the scattered light will be interpreted as absorbance.

In a preferred embodiment, the PDA integrates optical radiation over a specified time and converts the optical signal to a time multiplexed analog electronic signal called a scan where absorbance is calculated as:

| | |
|---|---|
| Absorbance$_i$= | log{(Reference Light$_i$-Reference Dark$_i$)/ (Sample Light$_i$-Sample Dark$_i$)} + log (ITS/ITR) |
| where Absorbance$_i$= | Absorbance pixel I |
| Reference Light$_i$= | Reference pixel I readings, with reference path open and sample path closed by a shutter; |
| Reference Dark$_i$= | Reference pixel I readings, with reference and sample paths closed by shutters; |
| Sample Light$_i$= | Sample pixel I readings, with sample path open and reference path closed by a shutter; |
| Sample Dark$_i$= | Sample pixel I readings, with sample and reference paths closed by shutters; |
| ITS= | integration time for sample measurement; |
| ITR= | integration time for reference measurement; |
| and | |
| I= | the particular pixel (wavelength) in the PDA. |

The electronic signal is proportional to the time that the detector integrates the optical signal. The electronic signal is amplified by analog electronic amplifiers and converted to a digital signal by an analog-to-digital converter or ADC. The digital information from the converter is interpreted for data analysis by a microprocessor 16 which is in turn connected via an RS232 connector to a computer 84. The results of the data analysis can be displayed on the computer 84, or on a printer (not shown in FIG. 1) connected to 84. A user can control the device through the computer 84, to specify a particular interferent to be analyzed and to determine the number and timing of measurements.

Although a rapid pre-screening device could take as much time as one to two minutes per sample measurement and still be considered rapid in this field of art, the present invention allows for rapid pre-screening of samples by taking successive sample measurements at intervals of 5 seconds for 4 interferents, (not including MB which will be measured after the MB is added to the plasma). After sample holder 22 is opened, the sample is placed according to a controlling process and a sensor in the sample holder activates the movable half of the holder to close when a sample is in place. Spectral data is collected after the holder is closed. Thereafter the sample is removed and another sample is picked up by the robotic arm and placed into the sample holder to allow for another measurement. This set of operations takes approximately 5 seconds.

The integration time for the sample beam is low for clear sample since there is less scattered light and therefore more light is transmitted to detector 78. When light is sufficiently scattered by, for example a turbid sample, spectrophotometer 14 automatically switches to a higher integration time. The higher integration time chosen will be within a preselected range, such that the detector's response is optimal. This feature will allow all samples, from the clearest to the most turbid, to be efficiently screened without exceeding the linear response range of the detector.

It is understood that this invention can be used with all varieties of tubing material as typically encountered in the blood bag industry.

As with any quantitative method, calibration of the spectrophotometer is required. However the method for NIR calibration is much more complex than most which can be calibrated with a minimum of a single standard material of known concentration. In respect of NIR calibration, samples must contain all interferents expected during the analysis of an unknown sample; the sample must contain an even distribution of the interferent of interest, and the concentrations of any two interferents should not correlate significantly. It is to be understood, that for any pre-screening, according to the present invention, of a typical sample for subsequent analysis, any combination of interferents may be present. The pre-screen allows for the determination of the concentration of any one in the presence or absence of the others.

The first part of a process for generating a calibration curve in order to practice the method of the present invention is to store spectral data for a calibration set. A calibration algorithm for each interferent is installed in a microprocessor so that when an unknown sample is tested for a particular interferent the result is quickly produced. In order to calculate the quantity of any interferent present, any one of several different methods, all of which are within the scope of this invention, may be used. For example, one approach is to process raw absorbance measurements by multiple linear regression and choosing wavelengths using standard procedures and statistics to find optimal wavelengths at which to describe concentrations of interferents. However significant changes in the spectrum brought about by lipemia, influence the outcome of calculations for haemoglobin or for bilirubin, or biliverdin, and consequently it is necessary to select additional wavelengths to compensate for these interactions.

Another method is to use all of the absorbance spectrum, and perform either a principal component analysis or partial least squares analysis and effectively determine from the components that are optimised, the concentration of these different elements. Unfortunately, these methods are computationally intensive and consequently take more time to calculate and increase the length of time required to assess each sample.

A preferred method is to calculate a first derivative of certain portions of absorbance spectra in respect of a particular interferent being measured. It is also possible to calculate the second, or third derivatives of absorbance, and such calculations are within the scope of this invention. However, each step of taking differences to calculate those derivatives is more time consuming and introduces more noise.

In practice, an optimal combination of first derivatives of at least two portions of an absorbance spectrum generated from a scan of a plasma specimen containing a particular interferent, is used to calculate interferent concentration. The precise approach used depends on the interferent being measured.

In respect of Hb results may be obtained by calculating the first derivative of absorbance measurements at wavelengths of approximately 591 nm and 653 nm. In respect of turbidity results may be obtained by calculating the first derivative of absorbance measurements at wavelengths of approximately 988 nm and 1038 nm, or for an alternative algorithm, 874 nm. In respect of bile pigments results may be obtained by calculating the first derivative of absorbance measurements at wavelengths of approximately 649 nm 731 nm and 907 nm for BV, and 504 nm, 518 nm and 577 nm for BR.

In respect of MB results may be obtained by calculating the first derivative of absorbance measurements at wavelengths of approximately 677 nm and 953 nm.

Since turbidity or lipemia is mainly due to chylomicron particles, turbidity may be simulated by adding IL to clear plasma; IL is an emulsion of fat particles similar to naturally-occurring chylomicrons.

Calibration equations outlined below cover a broad range of variability anticipated for the interferents. According to the present invention, if low-end accuracy becomes a concern, separate calibrations can be developed: one for the high end, and a second, if the result predicted by the previous calibration is less than a predetermined level.

To calibrate spectrophotometer for use in a preferred embodiment of the present invention, for haemoglobin, IL and BV, plasma specimens with normal appearance were spiked with 0 to 6 g/L Hb, 0 to 6.5 g/L IL, and 0 to 4.5 mg/dL BV. No significant intercorrelation among the analytes was allowed. The specimens were run once immediately after preparation, and then repeated using different segments of PVC tubing with random location of white markings on the surface of the tubing. Hb was prepared by replacing normal plasma (by appearance) with water and lysing erythrocytes through three freeze-thaw cycles. The Hb content of the supernatant of the lysate was measured on an Abbott Cell Dyn.™ The spectra were stored on diskettes. Analyses on sample sets were performed by a statistical computer program and algorithms developed for Hb, IL and BV. Independent sample sets were set aside for validation (referred to in the graphical representations as prediction) of the calibration equations. BR does not affect the measurements of Hb, IL and BV at their respective calibration wavelengths. Independent sample sets were set aside for validation (referred to in the graphical representations as prediction) of the calibration equations.

Figure 5:
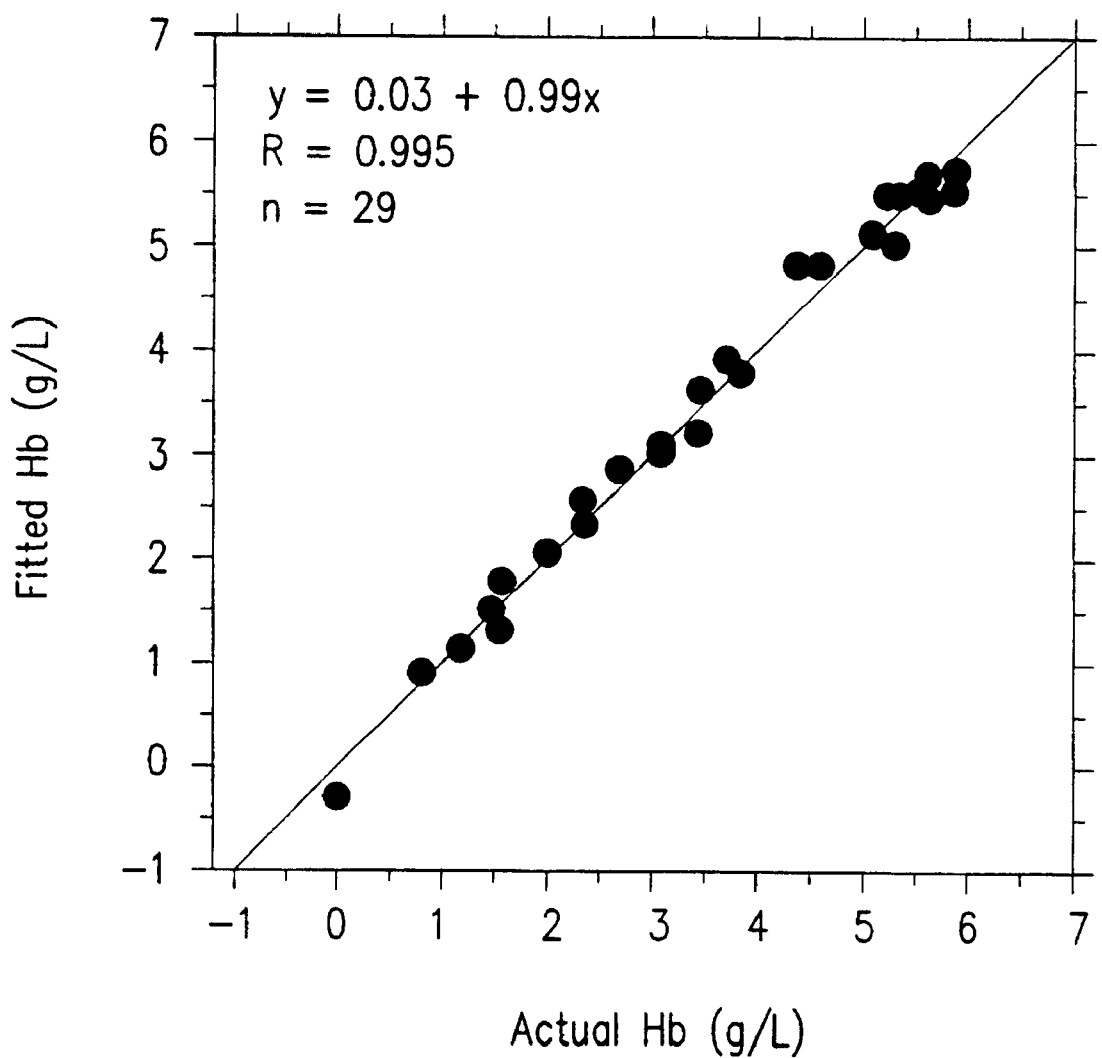
FIG. 5 is a graphic representation of a linear regression fit of data for haemoglobin calibration in units of grams per litre on the abscissa and ordinant axes.

FIG. 5 is a graphic representation of a linear regression fit of the data generated from the Hb calibration. The algorithm which was developed for Hb based on this data is as follows:

$$g/L\ Hb = 45.68(591\ nm) - 47.48(653\ nm) - 0.42$$

where (Tnm) is the first derivative of the absorbance measured at the wavelength specified.

Figure 6:
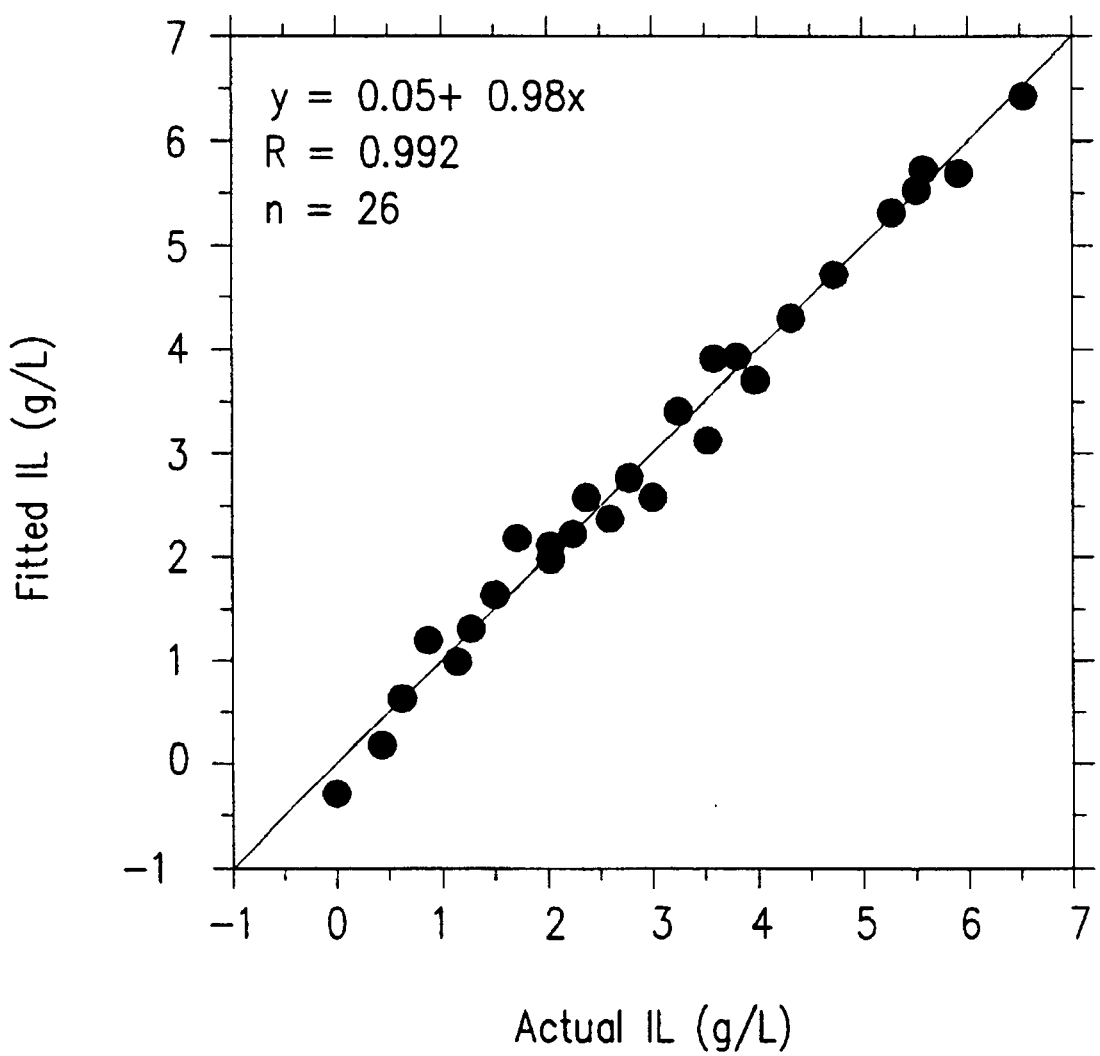
FIG. 6 is a graphic representation of a linear regression fit of data for turbidity calibration (using 988 nm and 1038 nm) in terms of intralipid concentration in units of grams per litre on the abscissa and ordinant axes.

FIG. 6 is a graphic representation of a linear regression fit of the data generated from the IL calibration. The algorithm which was developed for IL based on this data is as follows:

$$g/L\ IL = 432.42(988\ nm) + 40.40(1038\ nm) + 0.04$$

where (Vnm) is the first derivative of the absorbance measurement at the wavelength specified.

Figure 7:
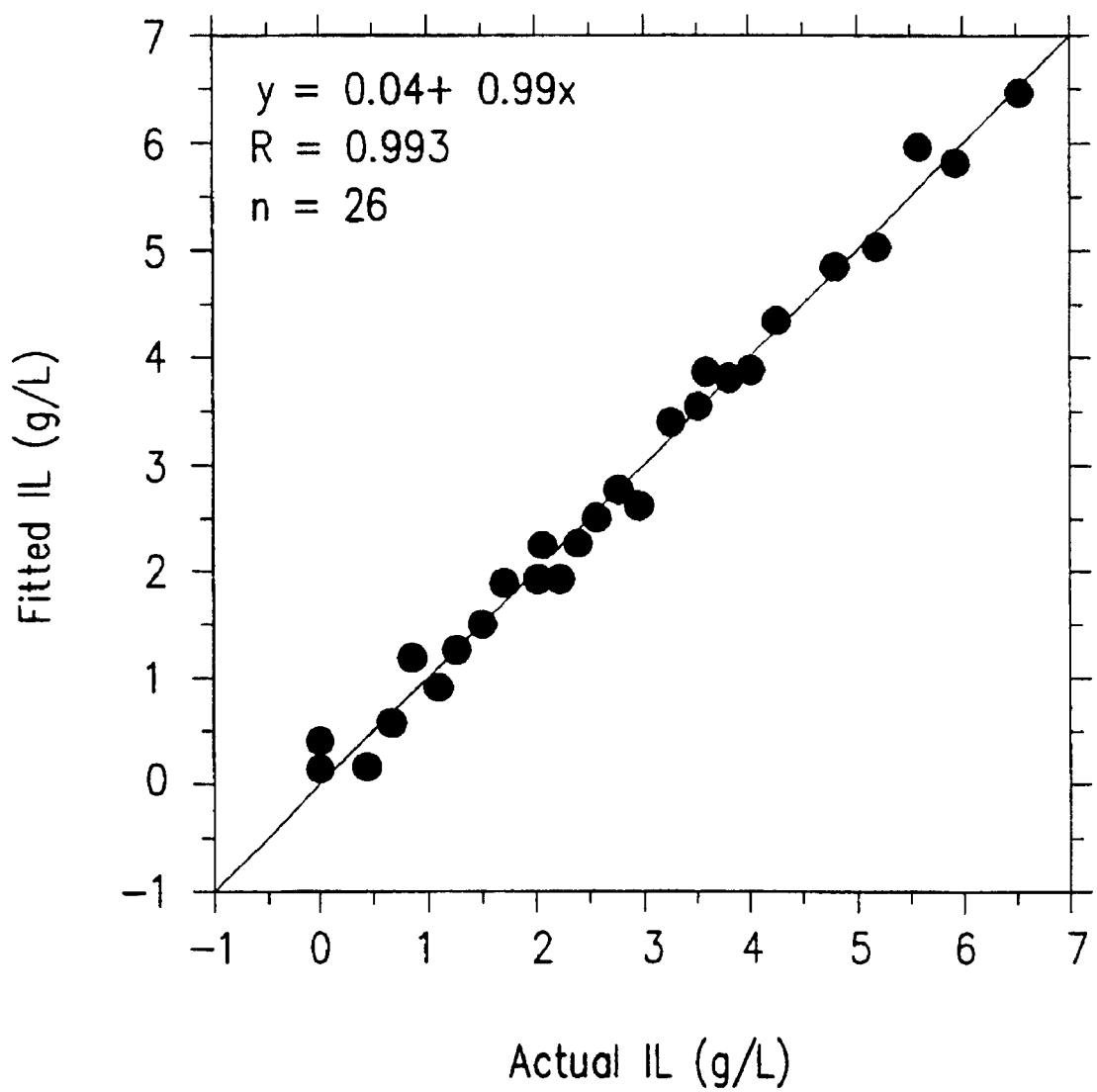
FIG. 7 is a graphic representation of a linear regression fit of data for turbidity calibration (using 874 nm ) in terms of intralipid concentration in units of grams per litre on the abscissa and ordinant axes.

FIG. 7 is a graphic representation of a linear regression fit of the data generated from another IL calibration. The alternative algorithm which was developed for IL based on this data is as follows:

$$g/L\ IL = 305.78(874\ nm) + 1.12$$

where (Wnm) is the first derivative of the absorbance measurement at the wavelength specified.

Figure 8:
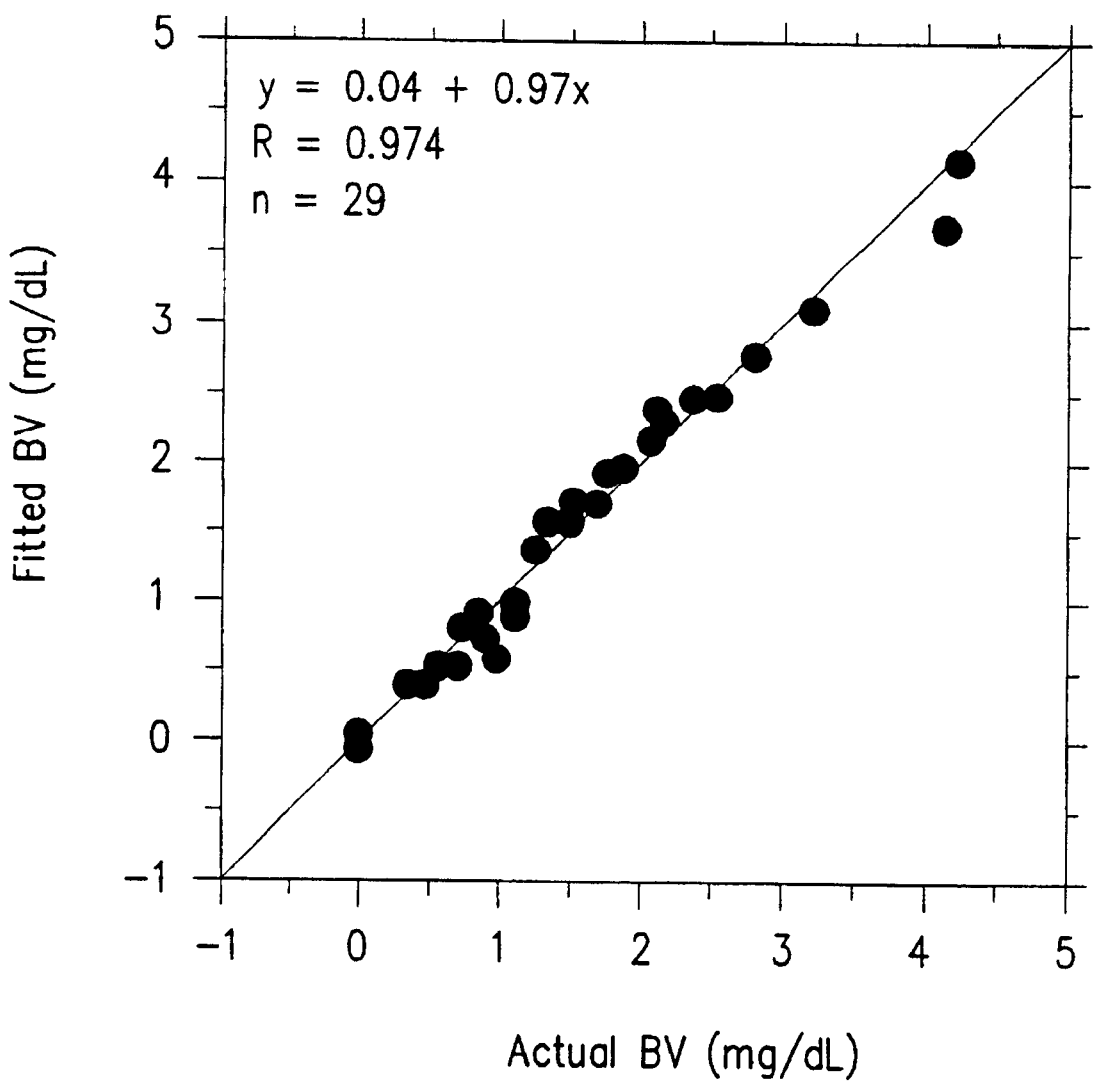
FIG. 8 is a graphic representation of a linear regression fit of data for biliverdin calibration in units of milligrams per decilitre on the abscissa and ordinant axes.

FIG. 8 is a graphic representation of the results of a linear regression fit of the data generated from the BV calibration. The algorithm which was developed for BV based on this data is as follows:

mg/dL BV=−45.40(649 nm)+323.15(731 nm)−493.79(907 nm)−1.14 where (Xnm) is the first derivative of the absorbance measurement at the wavelength specified.

In order to calibrate the spectrophotometer for BR, plasma specimens with normal appearance were spiked with 0 to 42 mg/dL Ditaurobilirubin (a synthetic conjugated bilirubin used to calibrate chemistry analyzers) 0 to 3 g/L Hb, 0 to 3 g/L IL, and 0 to 4 mg/dL BV. No significant intercorrelation among the analytes was allowed. The specimens were run once, immediately after preparation, and then repeated using different segments of PVC tubing with random location of white markings on the surface of the tubing. Hb was prepared by replacing normal plasma (by appearance) with water and lysing erythrocytes through three freeze-thaw cycles. Hb content of the supernatant of the lysate was measured on an Abbott Cell Dyn.™ The spectra were stored on diskettes. The analyses on sample sets were performed by a statistical computer program and algorithms developed for BR. Independent sample sets were set aside for validation (referred to in the graphical representations as prediction) of the calibration equations.

Figure 9:
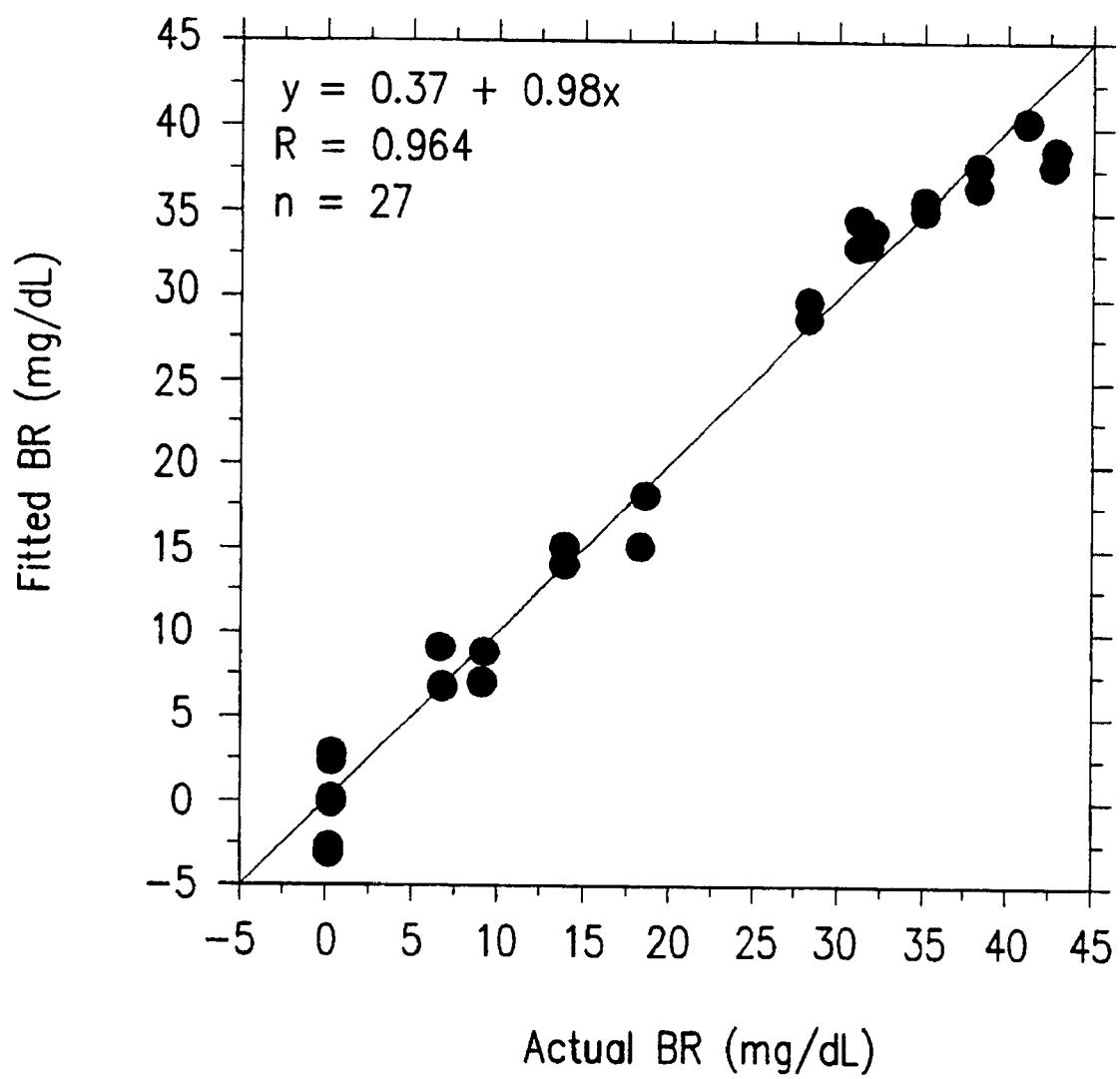
FIG. 9 is a graphic representation of a linear regression fit of data for bilirubin calibration in units of milligrams per decilitre on the abscissa and ordinant axes.

FIG. 9 is a graphic representation of the results of a linear regression fit of the data generated from the BR calibration. The algorithm which was developed for BR based on this data is as follows:

mg/dL BR=−43.03(504 nm)+252.11(518 nm)+240.03(577 nm)−2.89 where (Ynm) is the first derivative of the absorbance measurement at the wavelength specified.

To calibrate the spectrophotometer for methylene blue, plasma specimens with normal appearance (by appearance) were spiked with 0 to 860 μg/dL MB. MB is only added to plasma with normal appearance, therefore calibration for MB does not require the presence of the other interferents. The specimens were run once, immediately after preparation, and then repeated using different segments of PVC tubing with random location of white markings on the surface of the tubing. The spectra were stored on diskettes. The analyses on sample sets were performed by a statistical computer program and algorithms developed for MB. Independent sample sets were set aside for validation (referred to in the graphical representations as prediction) of the calibration equations. It should be understood that a calibration equation for MB in the presence of other interferents, can be developed according to the method of the present invention if necessary.

Figure 10:
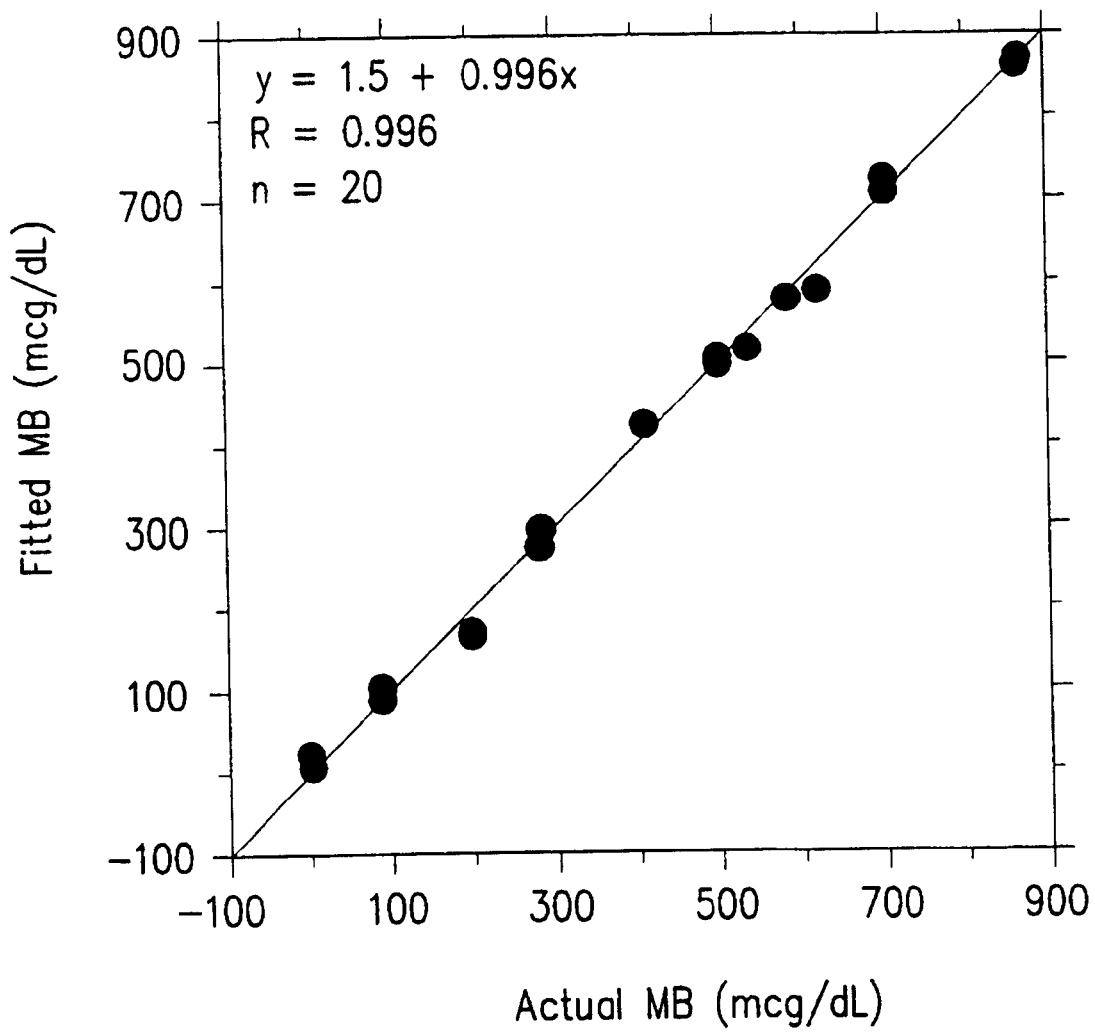
FIG. 10 is a graphic representation of a linear regression fit of data for methylene blue calculation in units of micrograms per decilitre (mcg/dL) on the abscissa and ordinant axes.
Figure 11:
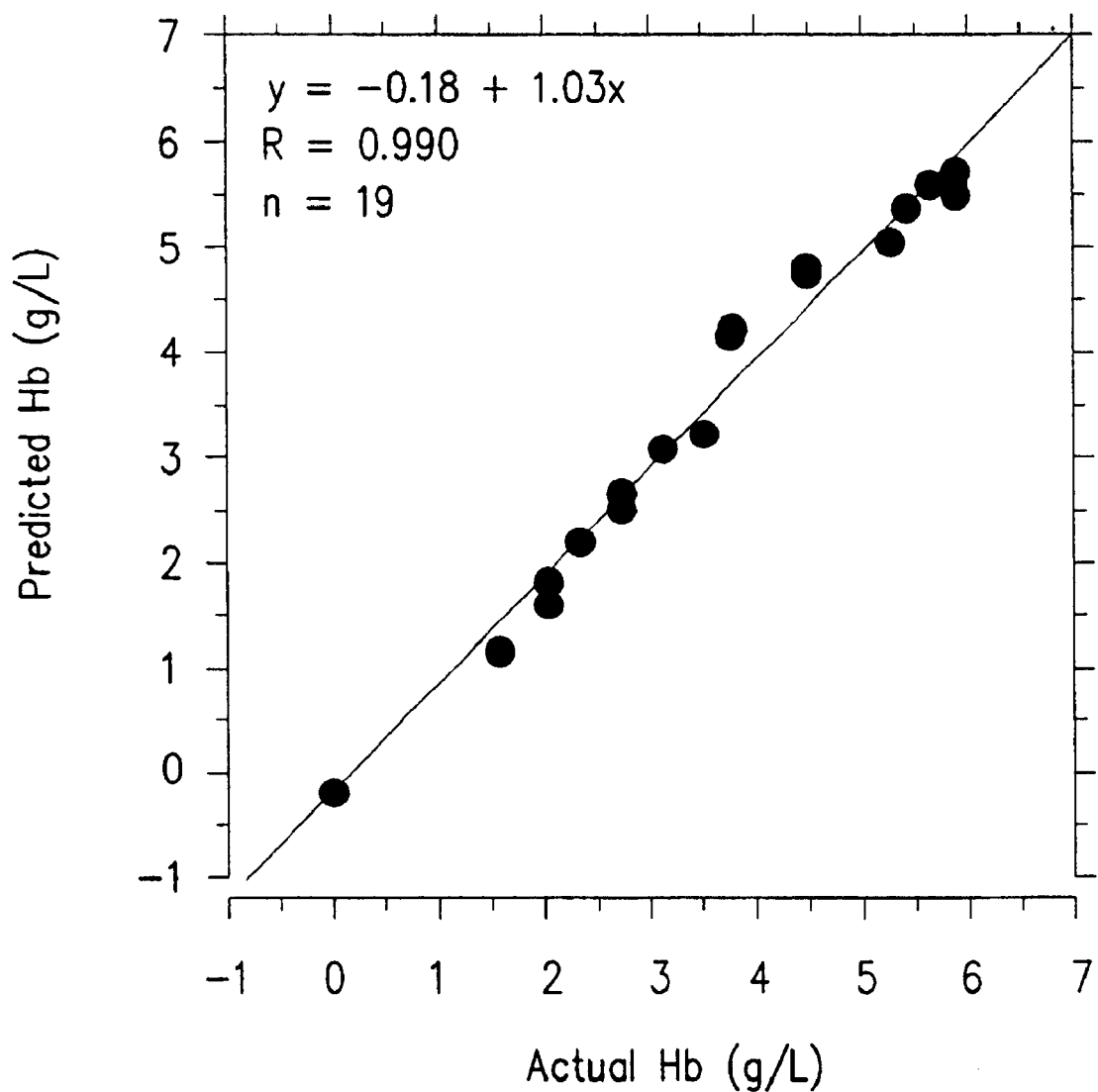
FIG. 11 is a graphic representation of a linear regression fit of data in respect of predicted haemoglobin concentration for samples not used in the calibration process, in units of grams per litre on the abscissa and ordinant axes.
Figure 12:
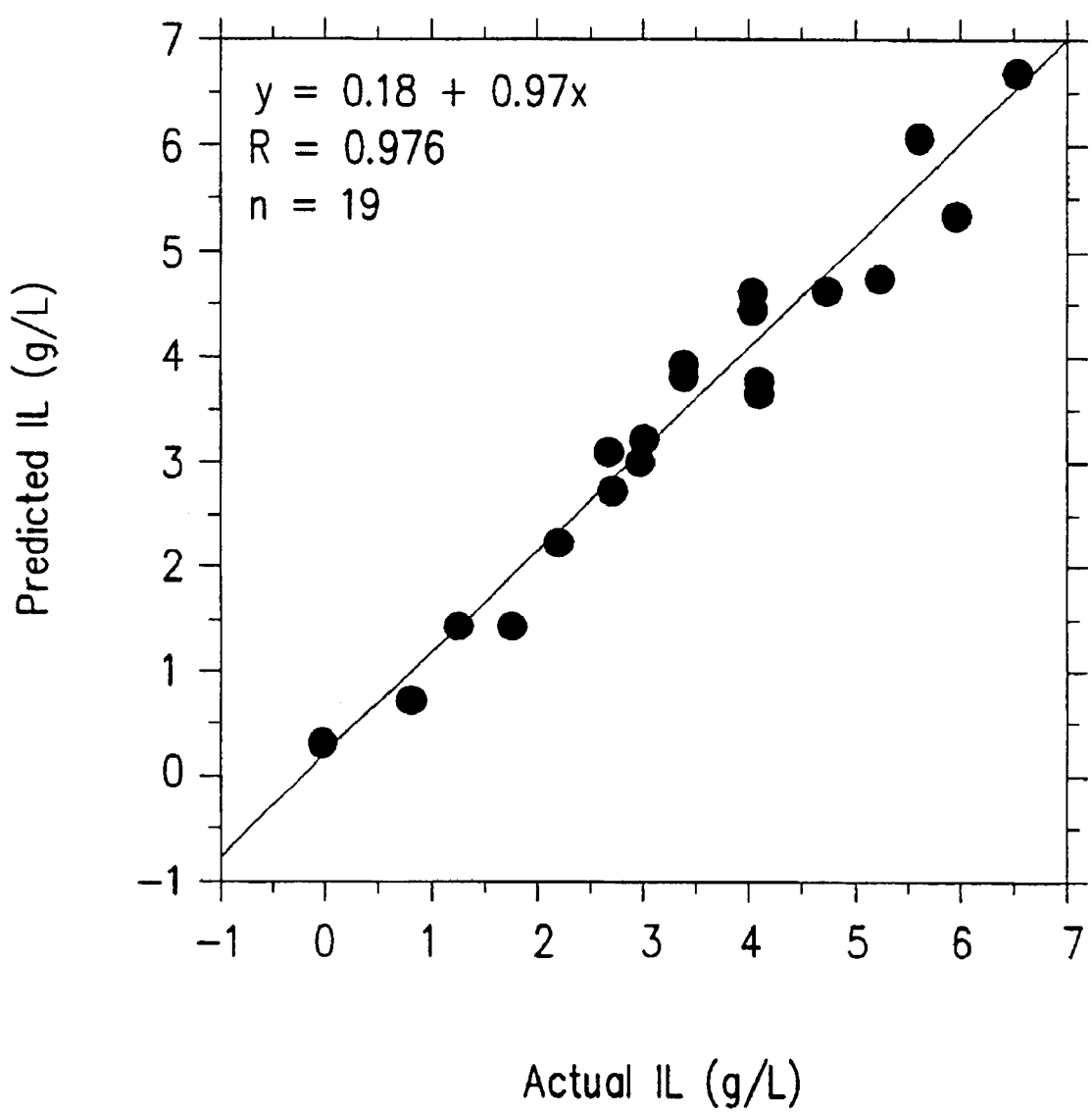
FIG. 12 is a graphic representation of a linear regression fit of data in respect of predicted intralipid concentration for samples not used in the calibration (using 988 nm and 1038 nm) process, in units of grams per litre on the abscissa and ordinant axes.
Figure 13:
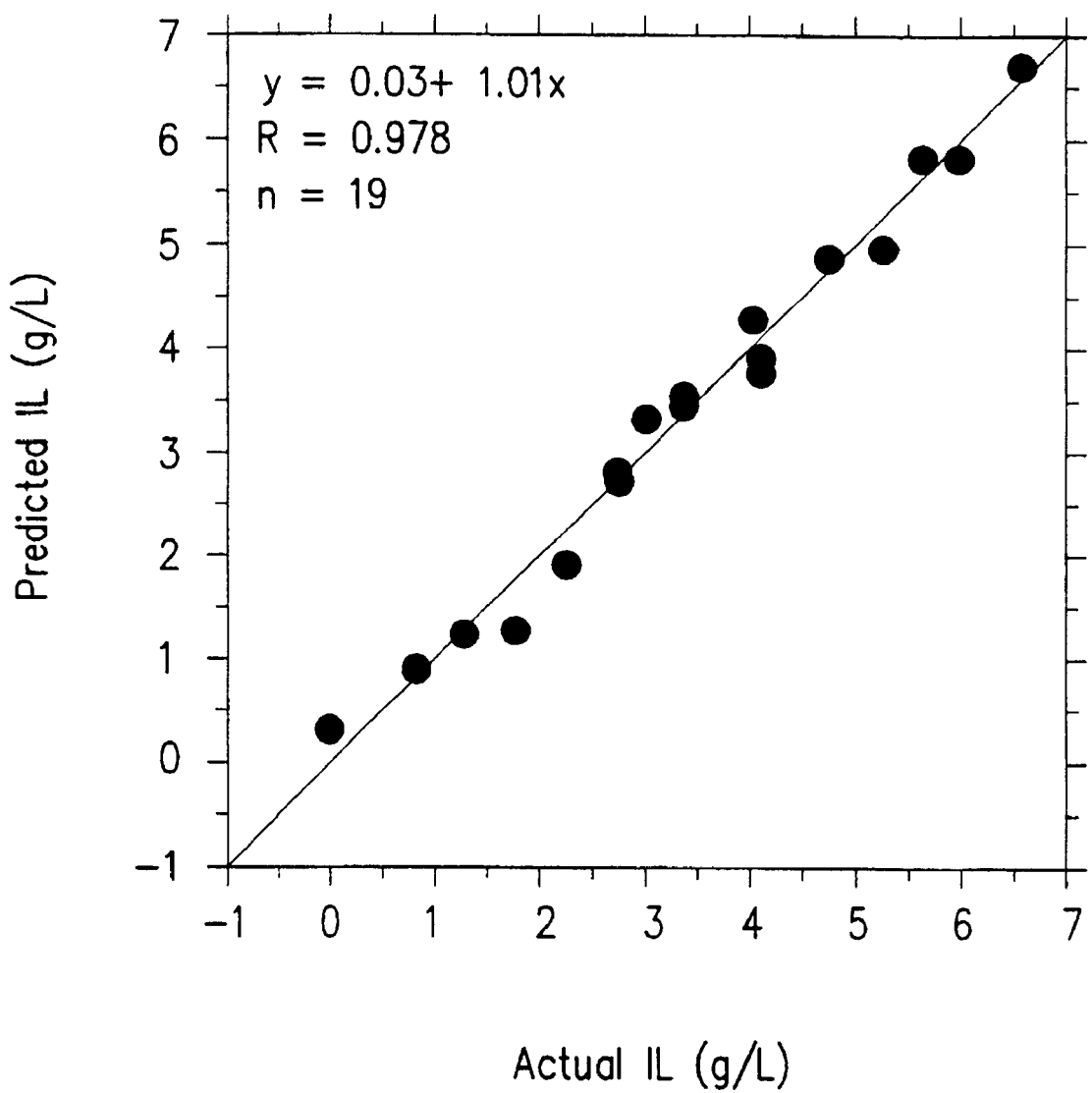
FIG. 13 is a graphic representation of a linear regression fit of data in respect of predicted intralipid concentration for samples not used in the calibration (using 874 nm) process, in units of grams per litre on the abscissa and ordinant axes.
Figure 14:
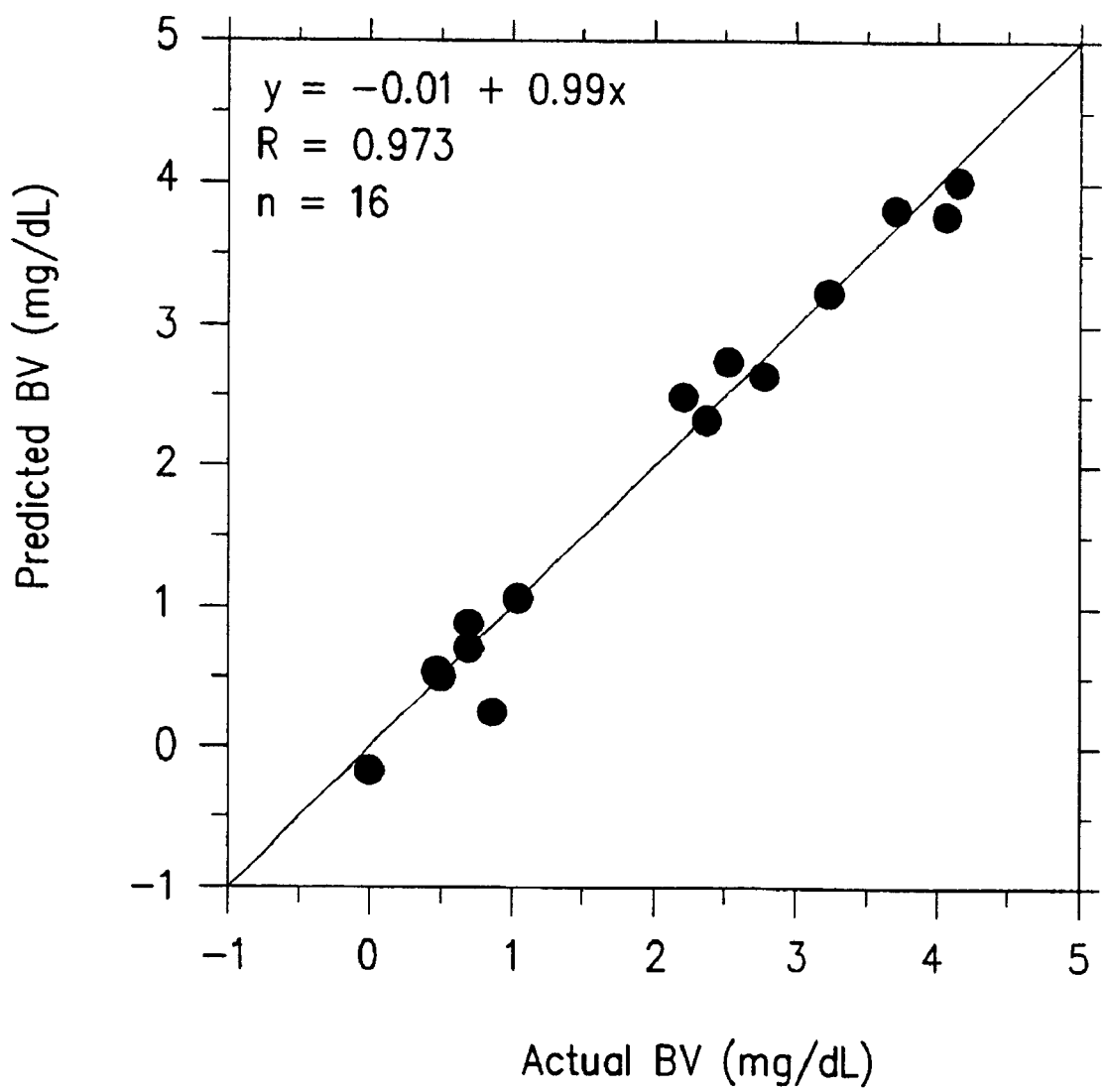
FIG. 14 is a graphic representation of a linear regression fit of data in respect of predicted biliverdin concentration for sample not used in the calibration process, in units of milligrams per decilitre on the abscissa and ordinant axes.
Figure 15:
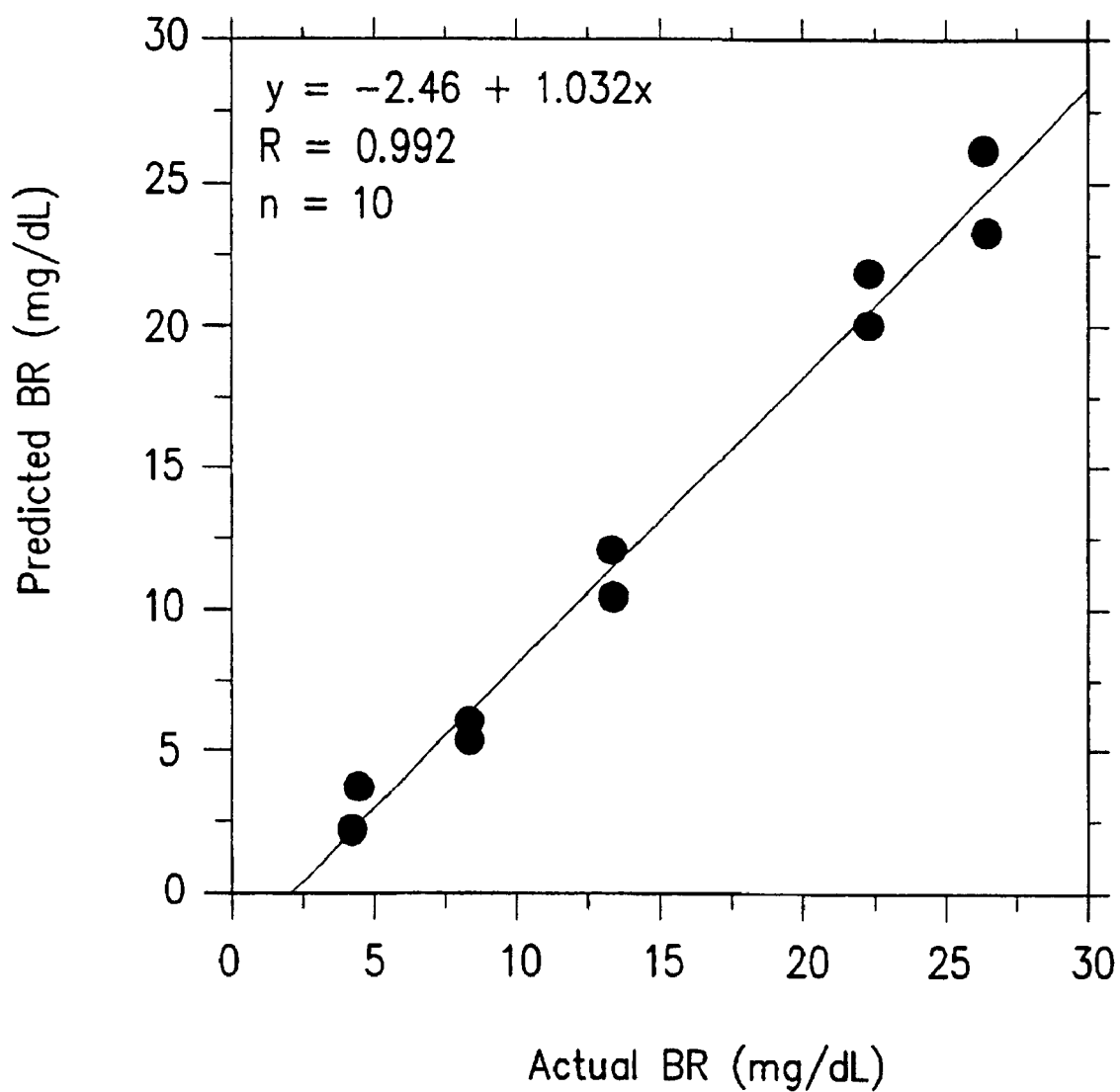
FIG. 15 is a graphic representation of a linear regression fit of data in respect of predicted bilirubin concentration for sample not used in the calibration process, in units of milligrams per decilitre on the abscissa and ordinant axes.
Figure 16:
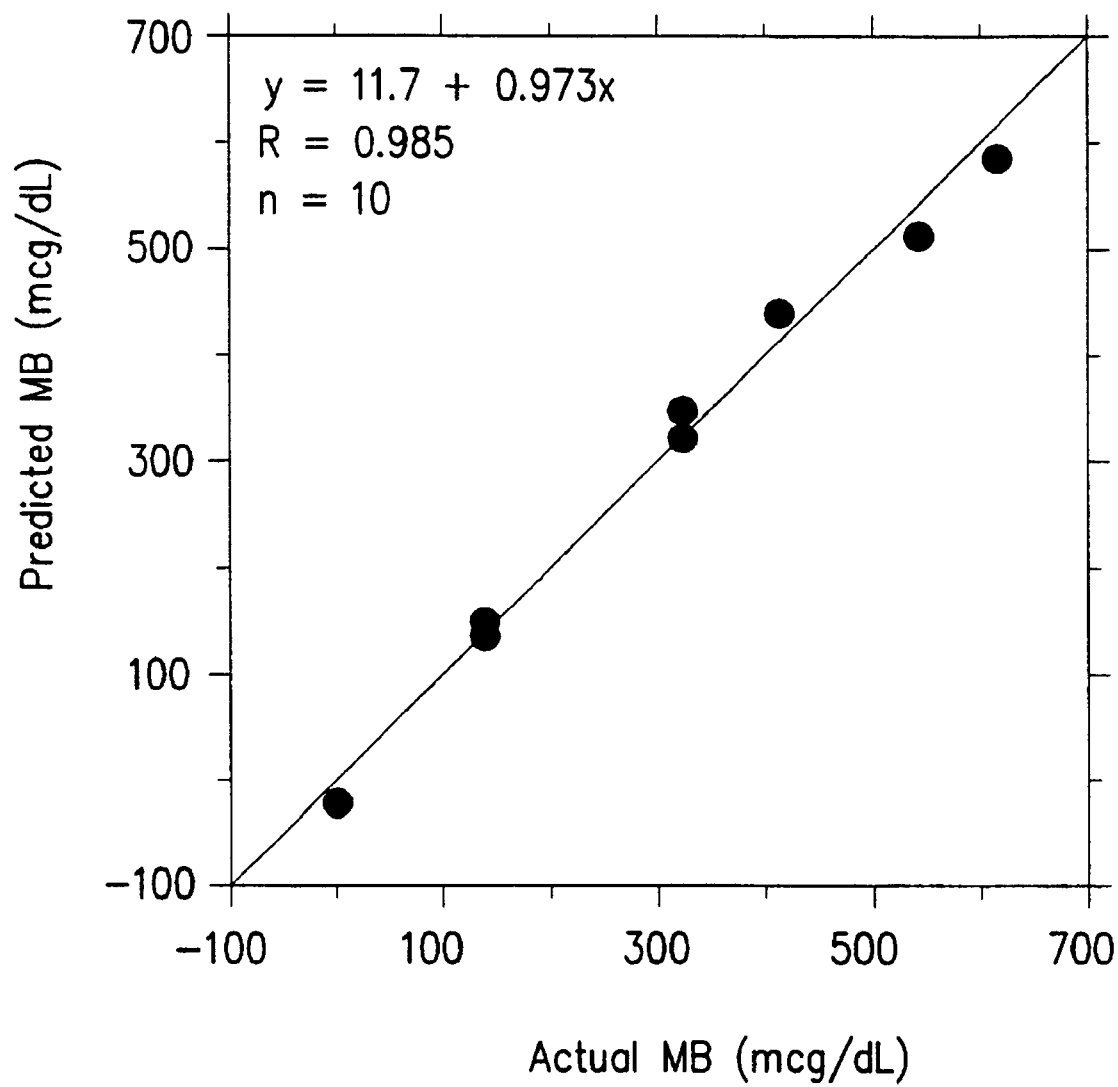
FIG. 16 is a graphic representation of a linear regression fit of data for predicted methylene blue concentration for samples not used in the calibration process, in units of micrograms per decilitre (mcg/dL) on the abscissa and ordinant axes.

FIG. 10 is a graphic representation of the results of a linear regression fit of the data generated from MB calibration. The algorithm which was developed for MB based on this data is as follows:

μg/dL MB=5603.5(677 nm)+26721.43(953 nm)+449.2 where (Znm) is the first derivative of the absorbance measurement at the wavelength specified.

FIGS. 11 to 16 are graphic representations of results of linear regression fits for predicted analyte concentrations for all five analytes for samples not used in the calibration processes; two were given for IL based on two different calibration algorithms.

As will be readily understood by those skilled in the art, several algorithms can be developed for each interferent using different groups of wavelengths with the resultant prediction performance by the different algorithms for the same interferent being similar.

While the invention has been particularly shown and described with reference to certain embodiments, it will be understood by those skilled in the art that various other changes in form and detail may be made without departing from the spirit and scope of the invention.

We claim:

1. An apparatus for determining the concentration of at least one interferent in plasma in tubing where said tubing connects containers of said plasma, the apparatus comprising:
   (A) a tubing holder comprising:
      (i) a stationary part having a cavity adapted to accept said tubing;
      (ii) a first optical fibre directed into said cavity positioned to transmit radiation into said tubing;
      (iii) a second optical fibre directed into said cavity positioned to receive radiation from said tubing, said first and second fibres being stationary and defining a constant fixed optical path length through said tubing and plasma across said cavity; and
      (iii) a lid which covers said cavity;
   (B) a lamp connected to said first fibre to provide said radiation;
   (C) a spectrophotometer to measure said received radiation from said second fibre; and
   (D) a computer means connected to said spectrophotometer for calculating a concentration of said at least one interferent based on said measurement to provide said concentration.

2. The apparatus of claim 1 wherein said computer means calculates said concentration by combining first derivatives of at least two portions of a spectrum generated from said measured radiation to provide said concentration.

3. The apparatus of claim 1 wherein the tubing is translucent and contains writing on its surface and the radiation is transmitted through the writing, tubing and the plasma contained in the tubing.

4. The apparatus of claim 1 wherein the optical fibres are positioned to measure reflectance of the radiation.

5. The apparatus of claim 2 where at the least one interferent in plasma is selected from the group consisting of haemoglobin, bilirubin, biliverdin, equivalent intralipid, and methylene blue.

6. An apparatus for determining the concentration of at least one interferent in plasma in a blood bag, the apparatus comprising:
   (A) a receptacle for receiving said bag, said receptacle comprising:
      (i) a cavity for receiving a corner of said blood bag, said cavity comprising two walls of fixed position which define a V-shaped receptor for said corner of said bag;
      (ii) a first optical fibre directed into said cavity positioned to transmit radiation into said bag;
      (iii) a second optical fibre directed into said cavity positioned to receive radiation from said bag, said first and second fibres being stationary and defining a constant fixed optical path length through said bag and plasma across said cavity;
   (B) a lamp connected to said first fibre to provide said radiation;

(C) a spectrophotometer to measure said received radiation from said second fibre; and (D) a computer means connected to said spectrophotometer for calculating a concentration of said at least one interferent based on said measurement to provide said concentration.

7. The apparatus of claim 6 wherein said computer means calculates said concentration by combining first derivatives of at least two portions of a spectrum generated from said measured radiation to provide said concentration.

8. The apparatus of claim 6 wherein said plasma bag is translucent and contains writing on its surface and said radiation is transmitted through said writing bag and said plasma.

9. The apparatus of claim 6 wherein the optical fibres are positioned to measure reflectance of the radiation.

10. The apparatus of claim 7 where said at least one interferent in plasma is selected from the group consisting of haemoglobin, bilirubin, biliverdin, equivalent intralipid, and methylene blue.

11. A method for determining the concentration of at least one interferent in plasma contained in two bags, said method comprising the steps of:

(A) providing a tubing and connecting said bags such that plasma can flow from said bags into said tubing;

(B) providing a lamp to irradiate said plasma in said tubing;

(C) providing means for directing radiation into said tubing and means for receiving radiation from said tubing such that a constant fixed optical path length is established between said means for directing and said means to receive radiation across said tubing and plasma;

(D) irradiating said tubing;

(E) providing a spectrophotometer to measure radiation from said tubing; and (F) calculating a concentration of said at least one interferent based on said measurement to provide said concentration.

12. The method of claim 11 wherein said calculation combines first derivatives of at least two portions of a spectrum generated from said measured radiation to provide said concentration.

13. The method of claim 11 wherein said tubing is translucent and contains writing on its surface and irradiation is transmitted through the writing, tubing and a plasma contained in the tubing.

14. The method of claim 11 wherein the radiation is reflected from a reflective surface placed behind the tubing.

15. The method of claim 12 wherein light leakages are compensated for by measuring dark current for both sample and reference measurements.

16. The method of claim 12 wherein the at least one interferent in plasma is selected from the group consisting of haemoglobin, bilirubin, biliverdin, equivalent intralipid, and methylene blue.

17. The method of claim 16 wherein absorbance is measured and such measurements are incorporated into the following algorithms for each of haemoglobin, bilirubin, biliverdin, equivalent intralipid, and methylene blue, respectively:

g/L HB=A (591 nm)−B (653 nm)−C where (Tnm) is a first derivative of the absorbance measured at the wavelengths specified and A, B, and C represent constants;

mg/dL BR=−A (504 nm)+B (518 nm)+C (577 nm)−D where (Ynm) is a first derivative of the absorbance measurements at the wavelengths specified and A, B, C, and D represent constants;

mg/dL BV=−A (649 nm)+B (731 nm)−C (907 nm)−D where (Xnm) is a first derivative of the absorbance measurement at the wavelengths specified and A, B, C, and D represent constants;

g/L IL=A (988 nm)+B (1038 nm)+C where (Vnm) is a first derivative of the absorbance measurement at the wavelengths specified and A, B, and C represent constants;

$\mu$g/dL MB=A (677 nm)+B (953 nm)+C where (Znm) is a first derivative of the absorbance measurement at the wavelengths specified and A, B and C represent constants; and in respect of each interferent calculating a concentration of said interferent in said plasma.

18. A method for determining the concentration of at least one interferent in plasma contained in a blood collection bag, the method comprising the steps of:

(A) providing a blood collection bag containing plasma;

(B) providing a lamp to irradiate said plasma in said bag;

(C) providing means for directing radiation into said bag; means for receiving radiation from said bag such that a constant fixed optical path length is established from said means to direct to said means to receive radiation across said bag and plasma;

(D) irradiating said bag;

(E) providing a spectrophotometer to measure radiation from said bag; and (F) calculating a concentration of said at least one interferent based on said measurement to provide said concentration.

19. The method of claim 18 wherein said calculation combines first derivatives of at least two portions of a spectrum generated from said measured radiation to provide said concentration.

20. The method of claim 18 wherein the bag is translucent and contains writing on its surfaces and said radiation is transmitted through said writing, wall and plasma contain in said bag.

21. The method of claim 18 wherein said radiation is measured and reflective surface placed behind the bag.

22. The method claim of claim 19 wherein said at least one interferent in plasma is selected from the group consisting of haemoglobin, bilirubin, biliverdin, equivalent intralipid, and methylene blue.

23. The method of claim 22 wherein absorbance is measured and such measurements are incorporated into the following algorithms for each of haemoglobin, bilirubin, biliverdin, equivalent intralipid, and methylene blue, respectively:

g/L HB=A (591 nm)−B (653 nm)−C where (Tnm) is a first derivative of the absorbance measured at the wavelengths specified and A, B, and C represent constants;

$$\text{mg/dL BR} = -A\,(504\text{ nm}) + B\,(518\text{ nm}) + C\,(577\text{ nm}) - D$$

where (Ynm) is a first derivative of the absorbance measurements at the wavelengths specified and A, B, C, and D represent constants;

$$\text{mg/dL BV} = -A\,(649\text{ nm}) + B\,(731\text{ nm}) - C\,(907\text{ nm}) - D$$

where (Xnm) is a first derivative of the absorbance measurement at the wavelengths specified and A, B, C, and D represent constants;

$$\text{g/L IL} = A\,(988\text{ nm}) + B\,(1038\text{ nm}) + C$$

where (Vnm) is a first derivative of the absorbance measurement at the wavelengths specified and A, B, and C represent constants;

$$\mu\text{g/dL MB} = A\,(677\text{ nm}) + B\,(953\text{ nm}) + C$$

where (Znm) is a first derivative of the absorbance measurement at the wavelengths specified and A, B+C represent constants; and in respect of each interferent calculating a concentration of said interferent in said plasma.

\* \* \* \* \*